(12) United States Patent
Moon et al.

(10) Patent No.: US 8,779,231 B2
(45) Date of Patent: Jul. 15, 2014

(54) TRANSGENIC MOUSE FOR EXPRESSING HUMAN FERRITIN IN TISSUE NON-SPECIFIC MANNER AND USE THEREOF

(75) Inventors: Woo Kyung Moon, Seoul (KR); Hoe Suk Kim, Seoul (KR)

(73) Assignee: SNU R&DB Foundation, Seoul (KR)

( * ) Notice: Subject to any disclaimer, the term of this patent is extended or adjusted under 35 U.S.C. 154(b) by 0 days.

(21) Appl. No.: 13/807,879

(22) PCT Filed: Jul. 7, 2011

(86) PCT No.: PCT/KR2011/004983
§ 371 (c)(1),
(2), (4) Date: Dec. 31, 2012

(87) PCT Pub. No.: WO2012/005529
PCT Pub. Date: Jan. 12, 2012

(65) Prior Publication Data
US 2013/0174284 A1   Jul. 4, 2013

(30) Foreign Application Priority Data
Jul. 7, 2010   (KR) .................. 10-2010-0065413

(51) Int. Cl.
*A01K 67/00* (2006.01)
*C12N 15/00* (2006.01)

(52) U.S. Cl.
USPC .............. 800/13; 435/320.1; 435/455; 800/8; 800/21

(58) Field of Classification Search
CPC .............. A01K 2267/03; A01K 2267/0393; A01K 2217/05; A01K 2227/105; C12N 2015/09
See application file for complete search history.

(56) References Cited

U.S. PATENT DOCUMENTS

2004/0259107 A1   12/2004 Ghetti et al.

OTHER PUBLICATIONS

Seo et al. Applied Microbial Biotechnol 2003;63:57-63.*
Jiang et al. Biochem Biophys Research Comm 2001;289;1088-92.*
Cai et al. J Cell Sci 2001;114Pt 12:2327-34.*
Cohen et al. Neoplast 2005;7:109-117.*
Hasegawa et al. Transgenic Res 2013;22:651-8.*
Hasegawa et al. Carcinogenesis 2012;33:2269-75.*
Ramalho, "Rapid degradation of dominant-negative Rab27 proteins in vivo precludes their use in transgenio mouse models." BMC Cell Biology 2002, 2(26): 1-17.
Hosokawa, "Regulation of Th2 Cell Development by Polycomb Group Gene bmi-1 through the Stabilization of GATA3." The Journal of Immunology 2006, 177:7656-7664.
Genove "A new transgene reporter for in vivo magnetic resonance imaging." Nature Medicine 2005, 11(4): 450-454.
Kim, "In vivo Imaging of Tumor Transduced with Bimodal Lentiviral Vector Encoding Human Ferritin and Green Fluorescent Protein on a 1.5T Clinical Magnetic Resonance Scanner." Cancer Research 2010, 10:7315-7324.
Cohen et al., "MRI detection of transcriptional regulation of gene expression in transgenic mice." Nature Medicine 2007, 13(4):498-503.

* cited by examiner

*Primary Examiner* — Janice Li
(74) *Attorney, Agent, or Firm* — Tanya A. Arenson; Casimir Jones, S.C.

(57) ABSTRACT

The present invention relates to a recombinant vector and a transgenic mouse for expressing human ferritin in a tissue non-specific manner, and more particularly, to a vector prepared by operably linking a human ferritin gene to a promoter including a cytomegalovirus (CMV) early enhancer element and a β-actin promoter, and a transgenic mouse expressing human ferritin in a tissue non-specific manner, which is transformed with the vector. Further, the present invention relates to a method for preparing a transgenic mouse, and a method for monitoring cell or tissue therapy using the transgenic mouse.

9 Claims, 10 Drawing Sheets

FIG. 2 pCAGGS-myc/hFTH #4 (CAG-f)
(Query : myc/hFTH 1731~2315,   Sbjct : sequencing data)

SEQ ID NO. 12
SEQ ID NO. 13

1. Lenti-myc-hFTH vector
2. pCAGGS vector
3. pCAGGS-myc-hFTH vector

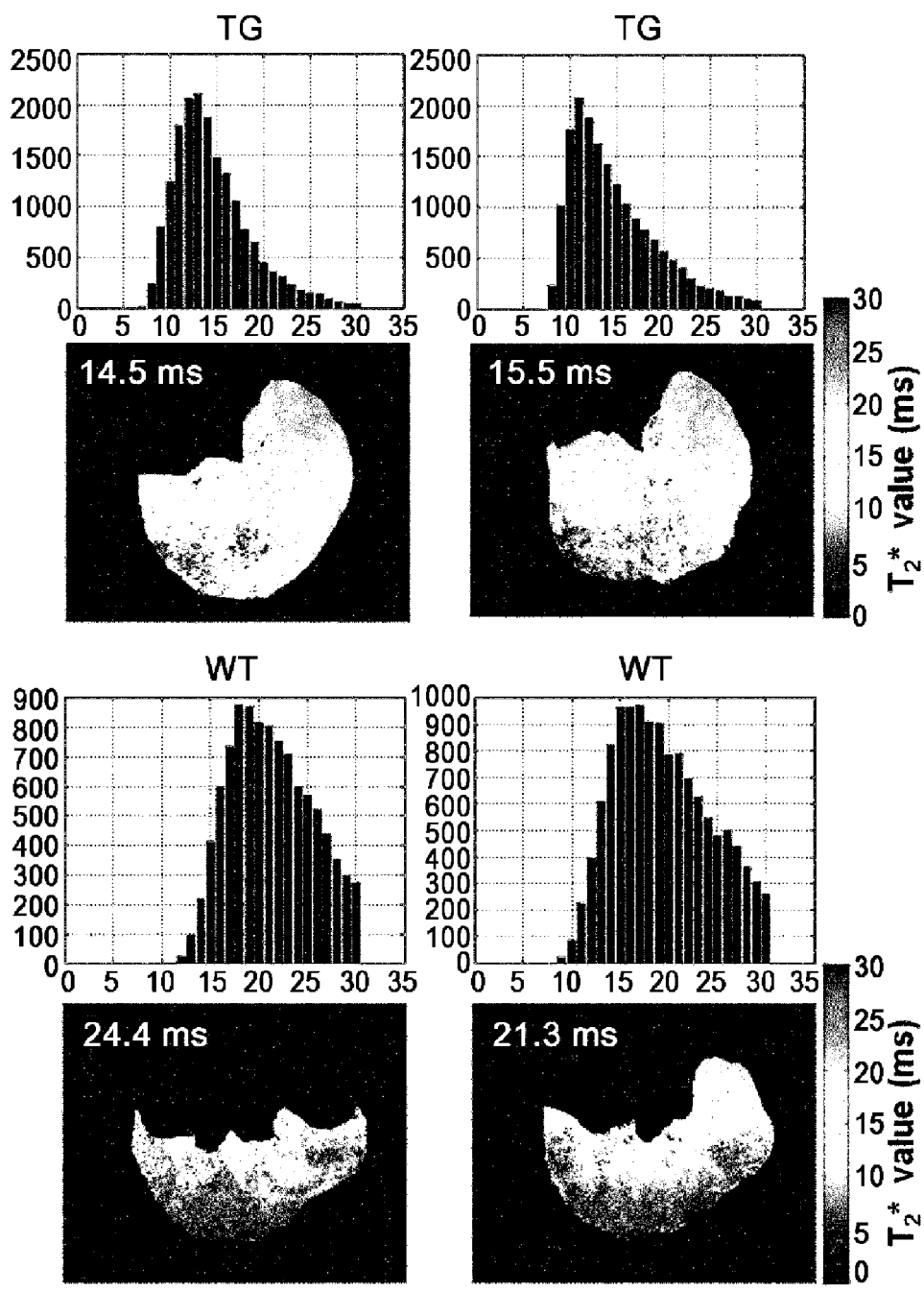

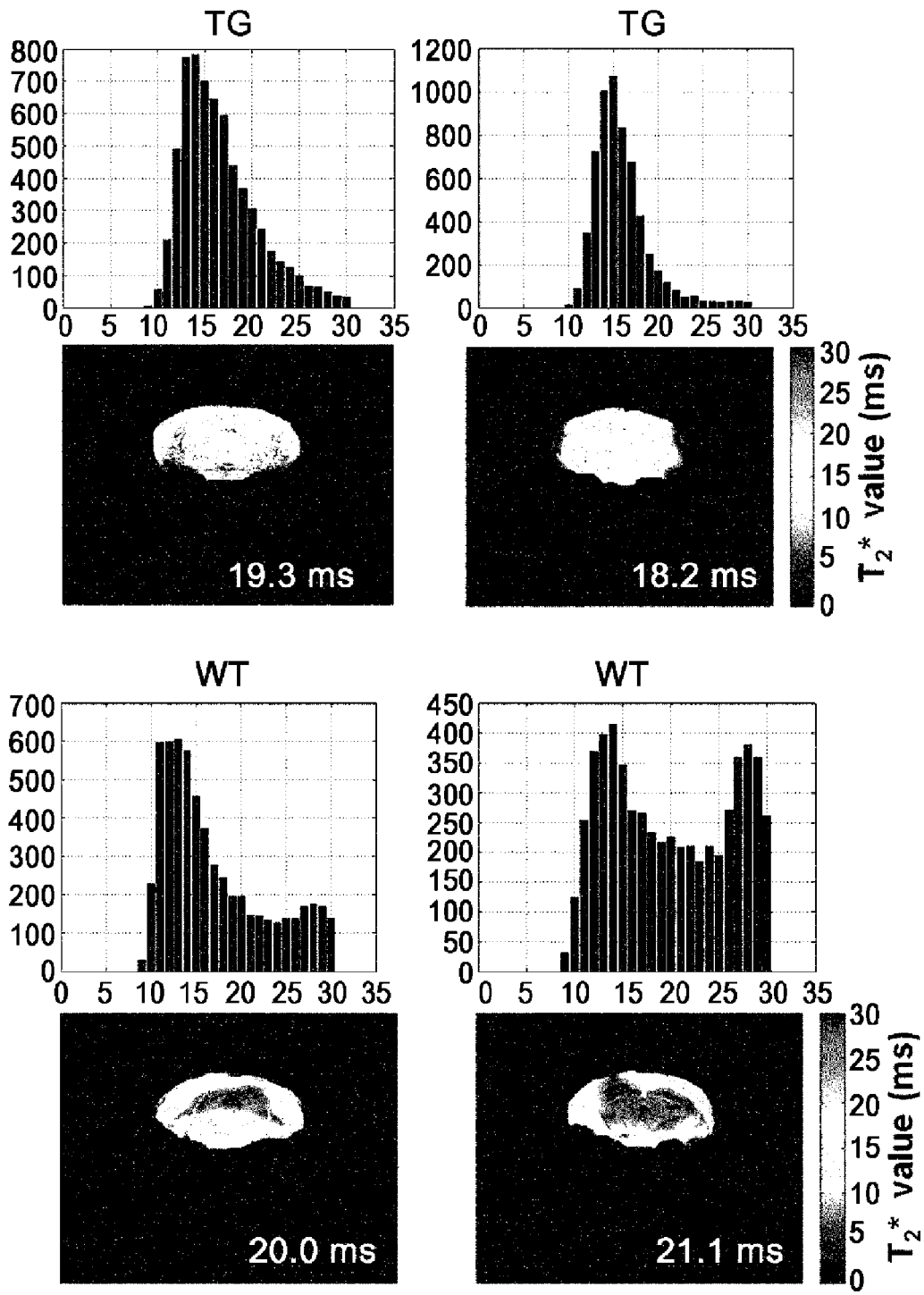

SEQUENCE LISTING

```
<160> NUMBER OF SEQ ID NOS: 13

<210> SEQ ID NO 1
<211> LENGTH: 597
<212> TYPE: DNA
<213> ORGANISM: Artificial Sequence
<220> FEATURE:
<223> OTHER INFORMATION: pCAGGS-myc/hFTH
<220> FEATURE:
<221> NAME/KEY: gene
<222> LOCATION: (12)..(44)
<223> OTHER INFORMATION: myc
<220> FEATURE:
<221> NAME/KEY: gene
<222> LOCATION: (45)..(596)
<223> OTHER INFORMATION: hFTH

<400> SEQUENCE: 1
aattcgccac catggaacaa aaactcatct cagaagagga tctgatgacg accgcgtcca     60
cctcgcaggt gcgccagaac taccaccagg actcagaggc cgccatcaac cgccagatca    120
acctggagct ctacgcctcc tacgtttacc tgtccatgtc ttactacttt gaccgcgatg    180
atgtggcttt gaagaacttt gccaaatact ttcttcacca atctcatgag gagagggaac    240
atgctgagaa actgatgaag ctgcagaacc aacgaggtgg ccgaatcttc cttcaggata    300
tcaagaaacc agactgtgat gactgggaga gcgggctgaa tgcaatggag tgtgcattac    360
atttggaaaa aaatgtgaat cagtcactac tggaactgca caaactggcc actgacaaaa    420
atgaccccca tttgtgtgac ttcattgaga cacattacct gaatgagcag gtgaaagcca    480
tcaaagaatt gggtgaccac gtgaccaact tgcgcaagat gggagcgccc gaatctggct    540
tggcggaata tctctttgac aagcacaccc tgggagacag tgataatgaa agctaag      597

<210> SEQ ID NO 2
<211> LENGTH: 23
<212> TYPE: DNA
<213> ORGANISM: Artificial Sequence
<220> FEATURE:
<223> OTHER INFORMATION: LentiM1.141-myc/hFTH F primer

<400> SEQUENCE: 2
cggaattcgc caccatggaa caa                                             23
```

```
<210> SEQ ID NO 3
<211> LENGTH: 26
<212> TYPE: DNA
<213> ORGANISM: Artificial Sequence
<220> FEATURE:
<223> OTHER INFORMATION: LentiM1.141-myc/hFTH R primer

<400> SEQUENCE: 3
cggaattctt agctttcatt atcact                                            26

<210> SEQ ID NO 4
<211> LENGTH: 20
<212> TYPE: DNA
<213> ORGANISM: Artificial Sequence
<220> FEATURE:
<223> OTHER INFORMATION: 1375F primer

<400> SEQUENCE: 4
cgcagggact tcctttgtcc                                                   20

<210> SEQ ID NO 5
<211> LENGTH: 20
<212> TYPE: DNA
<213> ORGANISM: Artificial Sequence
<220> FEATURE:
<223> OTHER INFORMATION: 1369R primer

<400> SEQUENCE: 5
acaacaacca gcacgttgcc                                                   20

<210> SEQ ID NO 6
<211> LENGTH: 20
<212> TYPE: DNA
<213> ORGANISM: Artificial Sequence
<220> FEATURE:
<223> OTHER INFORMATION: 1699F primer

<400> SEQUENCE: 6
aacgtgctgg ttgttgtgct                                                   20

<210> SEQ ID NO 7
<211> LENGTH: 20
<212> TYPE: DNA
<213> ORGANISM: Artificial Sequence
<220> FEATURE:
<223> OTHER INFORMATION: 2240R primer

<400> SEQUENCE: 7
cgtggtcacc caattctttg                                                   20

<210> SEQ ID NO 8
<211> LENGTH: 20
<212> TYPE: DNA
<213> ORGANISM: Artificial Sequence
<220> FEATURE:
<223> OTHER INFORMATION: 1743F primer

<400> SEQUENCE: 8
tcatctcaga agaggatctg                                                   20

<210> SEQ ID NO 9
<211> LENGTH: 21
<212> TYPE: DNA
<213> ORGANISM: Artificial Sequence
<220> FEATURE:
<223> OTHER INFORMATION: 2825R primer
```

<400> SEQUENCE: 9
gggacagcta tgactgggag t                                              21

<210> SEQ ID NO 10
<211> LENGTH: 20
<212> TYPE: DNA
<213> ORGANISM: Artificial Sequence
<220> FEATURE:
<223> OTHER INFORMATION: Myc-hFTH F primer

<400> SEQUENCE: 10
actcatctca gaagaggatc                                                20

<210> SEQ ID NO 11
<211> LENGTH: 20
<212> TYPE: DNA
<213> ORGANISM: Artificial Sequence
<220> FEATURE:
<223> OTHER INFORMATION: Myc-hFTH R primer

<400> SEQUENCE: 11
gctttcatta tcactgtctc                                                20

<210> SEQ ID NO 12
<211> LENGTH: 722
<212> TYPE: DNA
<213> ORGANISM: Artificial Sequence
<220> FEATURE:
<223> OTHER INFORMATION: pCAGGS-myc/hFTH

<400> SEQUENCE: 12 ttcttttcc tacagctcct gggcaacgtg ctggttgttg tgctgtctca tcattttggc     60
aaagaattcg ccaccatgga acaaaaactc atctcagaag aggatctgat gacgaccgcg   120
tccacctcgc aggtgcgcca gaactaccac caggactcag aggccgccat caaccgccag   180
atcaacctgg agctctacgc ctcctacgtt tacctgtcca tgtcttacta ctttgaccgc   240
gatgatgtgg cttgaagaa ctttgccaaa tactttcttc accaatctca tgaggagagg   300
gaacatgctg agaaactgat gaagctgcag aaccaacgag gtggccgaat cttccttcag   360
gatatcaaga aaccagactg tgatgactgg gagagcgggc tgaatgcaat ggagtgtgca   420
ttacatttgg aaaaaatgt gaatcagtca ctactgaac tgcacaaact ggccactgac   480
aaaaatgacc cccatttgtg tgacttcatt gagacacatt acctgaatga gcaggtgaaa   540
gccatcaaag aattgggtga ccacgtgacc aacttgcgca agatgggagc gcccgaatct   600
ggcttggcgg aatatctctt tgacaagcac accctgggag acagtgataa tgaaagctaa   660
gaattcactc tcaggtgca ggctgcctat cagaaggtgg tggctggtgt ggccaatgcc   720
ct                                                                 722

<210> SEQ ID NO 13
<211> LENGTH: 722
<212> TYPE: DNA
<213> ORGANISM: Artificial Sequence
<220> FEATURE:
<223> OTHER INFORMATION: pCAGGS-myc/hFTH

<400> SEQUENCE: 13 ttcttttcc tacagctcct gggcaacgtg ctggttgttg tgctgtctca tcattttggc     60
aaagaattcg ccaccatgga acaaaaactc atctcagaag aggatctgat gacgaccgcg   120

```
tccacctcgc aggtgcgcca gaactaccac caggactcag aggccgccat caaccgccag    180
atcaacctgg agctctacgc ctcctacgtt tacctgtcca tgtcttacta ctttgaccgc    240
gatgatgtgg ctttgaagaa ctttgccaaa tactttcttc accaatctca tgaggagagg    300
gaacatgctg agaaactgat gaagctgcag aaccaacgag gtggccgaat cttccttcag    360
gatatcaaga aaccagactg tgatgactgg gagagcgggc tgaatgcaat ggagtgtgca    420
ttacatttgg aaaaaaatgt gaatcagtca ctactggaac tgcacaaact ggccactgac    480
aaaaatgacc cccatttgtg tgacttcatt gagacacatt acctgaatga gcaggtgaaa    540
gccatcaaag aattgggtga ccacgtgacc aacttgcgca agatgggagc gcccgaatct    600
ggcttggcgg aatatctctt tgacaagcac accctgggag acagtgataa tgaaagctaa    660
gaattcactc ctcaggtgca ggctgcctat cacaaggtgg cggctggtgt ggccaatgcc    720
ct                                                                  722
```

US 8,779,231 B2

TRANSGENIC MOUSE FOR EXPRESSING HUMAN FERRITIN IN TISSUE NON-SPECIFIC MANNER AND USE THEREOF

CROSS REFERENCE TO RELATED APPLICATIONS

The present application is a national phase application under 35 U.S.C. §371 of PCT International Application No. PCT/KR2011/004983, filed on Jul. 7, 2011, which claims the benefit of Korean Patent Application No. 10-2010-0065413, filed on Jul. 7, 2010, each of which are herein incorporated by reference in its entirety.

BACKGROUND OF THE INVENTION

1. Field of the Invention

The present invention relates to a recombinant vector and a transgenic mouse for expressing human ferritin in a tissue non-specific manner, and more particularly, to a vector prepared by operably linking a human ferritin gene to a promoter including a cytomegalovirus (CMV) early enhancer element and a β-actin promoter, and a transgenic mouse for expressing human ferritin in a tissue non-specific manner, which is transformed, with, the vector. Further the present invention relates to a method for generating a transgenic mouse, and a method for monitoring cell or tissue therapy using the transgenic mouse.

2. Description of the Related Art

Ferritin is a bioactive molecule present in the liver, spleen, and bone marrow of mammals. Ferritin, first isolated from the spleen and liver of horse by Lauflberger in 1937, is composed of 24 protein subunits surrounding a central iron core (diameter: 120-130 A.U., inner cavity diameter: 75 A.U.) according to X-Ray and electron microscopy. That is, each ferritin molecule is composed of a spherical protein shell with an average molecular weight of 450,000, called apoferritin, which consists of 24 protein subunits with a molecular weight of approximately 19,000 and contains 20~30% Fe as a ferric hydroxyphosphate polymer form. Thus, ferritin is a physiological active molecule as a sole source of iron which is released from the protein and utilized in the body when demanded. When fully loaded with Fe, ferritin can store up to 4,500 iron atoms per molecule, which is equivalent to an iron concentration capable of producing 1200 hemoglobin molecules.

Meanwhile, ferritin, the iron storage protein essential for life, was recently suggested to be a candidate reporter for the detection of gene expression by magnetic resonance imaging (MRI). Ferritin is a metalloprotein containing iron atoms, and thus functions as a nanomagnet to be utilized as an MRI reporter. Relying on signals derived from hydrogen protons produced by water-molecules exposed to a magnetic field, regular MRI converts the signals into images. In ferritin-applied MRI, however, the nanomagnet directly stimulates surrounding protons to generate signals. Therefore, ferritin allows non-invasive MRI without injection of coutrast agents.

The ferritin heavy polypeptide subunit (FTH) has a potent, ferroxidase activity that catalyzes the oxidation of ferrous iron. The magnetic resonance (MR) properties of FTH were the focus of extensive research and showed abnormality with high relaxivity at very low iron loading on the magnetic field. The overexpression of FTH could augment $R_2$ relaxivity upon magnetic resonance imaging (MRI) by redistribution of iron among more ferritin complexes as well as by increased total cellular iron level.

It was reported that the TET-mFTH transgenic mice overexpressing HA-tagged mouse FTH and EGFP (enhanced green fluorescent protein) were generated in a tissue specific and tetracycline inducible manner by using the MR properties of ferritin (Cohen, B., Ziv, K., Plaks, V., Israely, T., Kalchenko, V., Harmelin, A., Benjamin, L. E. and Neeman, M. (2007). MRI detection of transcriptional regulation of gene expression in transgenic mice, Nat Med 13, 498-503.). The above report suggested the possibility for MR application of ferritin as a reporter gene in multiple organs and the safety of chronic overexpression of FTH for applications for long-term tracking. According to the known technologies, however, ferritin cannot be applied to MR imaging of multiple organs because of its tissue specific expression, and there is also no report on the technologies of expressing the ferritin gene in a tissue non-specific manner.

The present inventors have made an effort to find a technology for expressing the ferritin gene in a tissue non-specific manner. As a result, they developed the transgenic mouse (C5BL/6-β-actin-hFTH) expressing human ferritin (hFTH) under the control of ubiquitous CAG promoter, which allows broader expression. The hFTH expression was detected in most tissue such as the brain, heart, liver, lung, spleen, pancreas and kidney by RT-PCR and Western blot. The histological changes in tissues with overexpression of hFTH were not detected. They evaluated hFTH expression as a functional MR reporter by performing noninvasive magnetic resonance imaging (MRI) of transgenic mice using 9.4 T. Expression of the hFTH in the brain and liver tissues of mice leads to a significant decrease in T2* relaxation time. Based on this study, the present inventors also demonstrated that hFTH can be used as an MR reporter and the transgenic mice of the present invention would be an available model of hFTH-based molecular imaging to study potential therapies for the cell and tissue graft, thereby completing the present invention.

SUMMARY OF THE INVENTION

An object of the present invention is to provide a recombinant vector for expressing human ferritin in a tissue non-specific manner, which is prepared by operably linking a human ferritin gene to a promoter including a cytomegalovirus (CMV) early enhancer element and a β-actin promoter.

Another object of the present invention is to provide a transgenic mouse for expressing human ferritin in a tissue non-specific manner, which is transformed with the vector, or a cell or tissue isolated therefrom.

Still another object of the present invention is to provide a method for generating a transgenic mouse for expressing human ferritin in a tissue non-specific manner, comprising the steps of 1) preparing a vector including a cytomegalovirus early enhancer, a β-actin promoter, and a human ferritin; and 2) transfecting fertilized eggs with the expression vector.

Still another object of the present invention is to provide a method for monitoring cell or tissue therapy using the transgenic mouse.

BRIEF DESCRIPTION OF THE DRAWINGS

FIG. 2 is the result of sequence analysis of myc-hFTH gene, in which the cloned cDNA of myc-hFTH gene was inserted at 1720-2317 of pCAGGS vector, and the EcoRI recognition Sites are underlined, myc is indicated, by the shaded boxes, hFTH is indicated by arrows, and the myc-hFTH gene cleaved with EcoRI is represented by SEQ ID NO. 1;

FIG. 9 shows the color-coded T2*-weighted images of the liver and brain from myc-hFTH transgenic mouse and age- and sex-matched wild-type mouse on 9.4 T, in which myc-hFTH transgenic mice showed hypo-intense signals (low T2* values) in the liver (a) and the brain (b) compared, with the wild-type mice.

DETAILED DESCRIPTION OF THE PREFERRED EMBODIMENTS

In one embodiment to achieve the above objects, the present invention provides a recombinant vector for expressing human ferritin in a tissue non-specific manner, which is prepared, by operably linking a human ferritin gene to a promoter including a cytomegalovirus (CMV) early enhancer element and a β-actin promoter.

Figure 1:
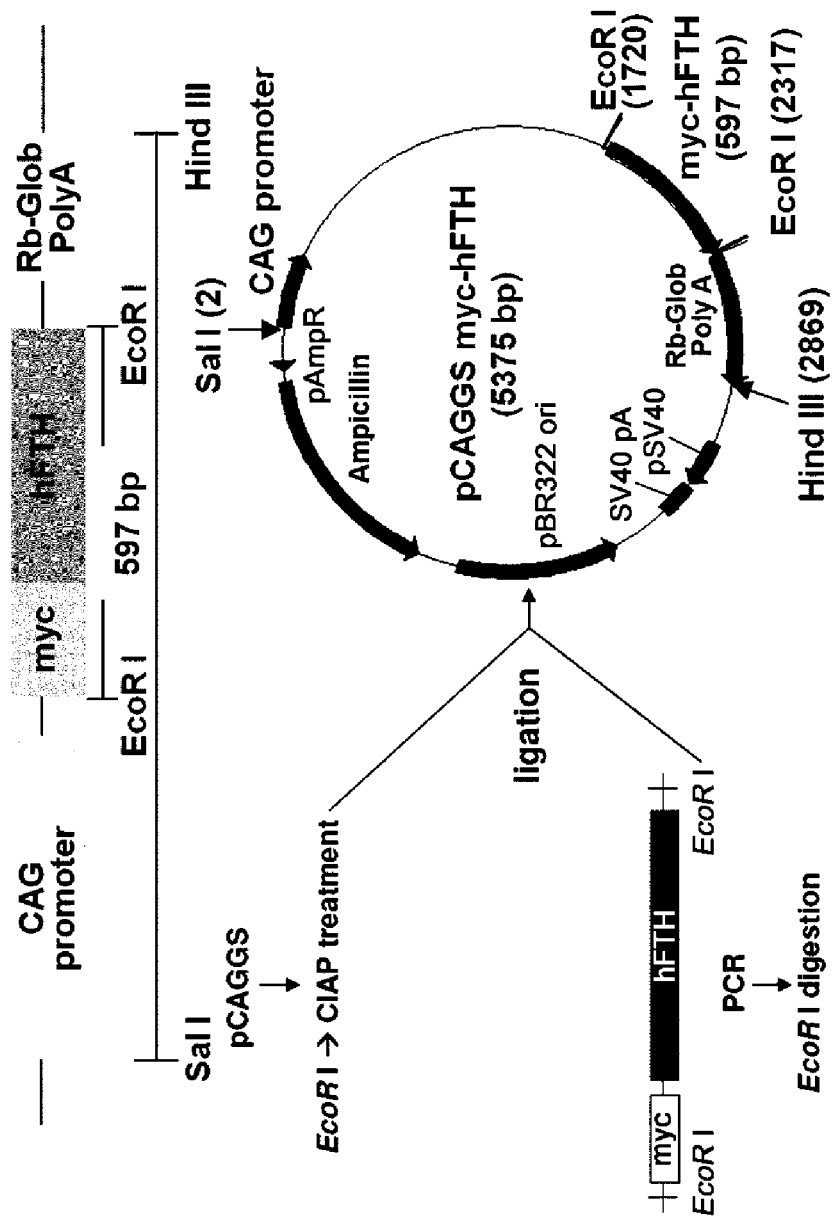
FIG. 1 shows construction of the recombinant human ferritin heavy polypeptide for myc-hFTH transgenic mice generation, in which a pCAGGS-myc-hFTH was constructed for myc-hFTH transgenic mice, and the 2,867 bp Sal I/HindII fragment was used for microinjection.

Preferably, the vector may be a vector represented by a cleavage map of FIG. 1.

As used herein, the term "promoter" refers to a DNA sequence capable of controlling the transcription of the nucleotide sequence of interest into mRNA, when ligated to a nucleotide sequence of interest. Typically, a promoter is though not necessarily, located 5' (i.e., upstream) of a nucleotide sequence of interest whose transcription into mRNA it controls, and provides a site for specific binding by RNA polymerase and other transcription factors for initiation of transcription. The promoter of the present invention is a constitutive promoter. The term "constitutive" when made in reference to a promoter means that the promoter is capable of directing transcription of an operably linked nucleic acid sequence in the absence of a stimulus (e.g., heat shock, chemicals, etc.). The prompter of the present invention may be preferably a CAG promoter. The CAG prompter is, one of the modified CMV promoters, a hybrid promoter including a cytomegalovirus early enhancer, a chicken β-actin promoter, a chimeric intron, exon 1 and a part of exon 2 of a rabbit β-globin gene (Hitoshi Niwa et al., Gene, 108:198-199, 1931, Monahan et al., Gene Therapy, 7:24-30, 2000), but it can be variously modified according to the purpose.

As used herein, the term "operably linked" refers to a functional linkage between a nucleic acid sequence coding for a target protein or RNA and a nucleic acid expression control sequence in such a manner as to allow general functions. For example, a promoter is operably linked to a protein or RNA-coding nucleic acid, sequence, which affects expression of the coding nucleic acid sequence. The operable linkage to a recombinant vector may be prepared, using a genetic recombinant technique well known in the art, and site-specific DNA cleavage and ligation may be achieved using enzymes generally known in the art.

As used, herein, the term "recombinant vector", which describes a vector capable of expressing a protein or RNA of interest in a suitable host cell, refers to a genetic construct that comprises essential regulatory elements to which a gene insert, is operably linked in such a manner as to be expressed in a host cell. Preferably, the recombinant vector represented, by the cleavage map of FIG. 1 includes the base sequence represented, by SEQ ID NO. 1. The base sequence of SEQ ID NO. 1 is a myc-tagged hFTH gene, and contains EcoRI restriction enzyme site, which may be inserted before the cleavage (FIG. 2).

As used herein, the term "ferritin" gene-expressing ferritin protein is an iron storage protein, and traps intracellular irons. When the ferritin protein is expressed in cells, iron molecules sequestered in the expressed ferritin protein display magnetic properties. Thus, an additional compound as an MRT contrast agent is not needed, and cells are able to produce their own substances for MRI, thereby achieving MRI detection without limitation of a blood barrier. As used, herein, the term, "for MRI contrast" means that the contrast between cells and surrounding tissues is enhanced to facilitate MRI (magnetic resonance imaging) detection, which can be achieved by expressing the vector of the present invention in cells as an MRI contrast agent.

The ferritin protein, of the present invention may be an intact ferritin protein having both light and heavy chains, or may be a ferritin heavy chain, preferably a ferritin heavy chain. Ferritin iron binding is catalyzed, by the ferritin heavy chain in the ferritin protein, and thus ferritin heavy chain is only used, to retain iron-binding ability while having a lower molecular weight.

The ferritin protein of the present invention may be derived from animals including human, plants, bacteria and fungi, preferably human, and more preferably human ferritin heavy chain.

In addition, the ferritin protein of the present invention may be labeled with a tag, as long as it does not inhibit iron-binding ability. A tag sequence may be preferably added at C- or N-terminal of the nucleic acid molecule encoding the ferritin protein of the present invention. As used herein, the term, "tag" or "tag sequence" refers to a chemical moiety, either a nucleotide, oligonucleotide, polynucleotide or an amino acid, peptide or protein or other chemical, that when added to another, sequence, provides additional utility or confers useful properties, particularly in the detection or isolation, to that sequence. In the case of protein tags, histidine residues may be added to either the amino- or carboxy-terminus of a protein to facilitate protein detection, selection or isolation. Alternatively, epitopes representing reactive with specific antibody or amino acid sequences, peptides, proteins which are binding determinants or fusion partners or other molecules, for example, influenza A virus hemagglutinin protein, protein A, cellulose binding domain, calmodulin binding protein, maltose binding protein, chitin binding domain, glutathione S-transferase and analogs thereof, FLAG epitope, c-myc epitope, transmembrane epitope, may be added to proteins to facilitate protein, isolation, localization, and detection by procedures such as affinity or immunoaffinity chromatography, and immunohistochemistry.

In the present invention, the gene of myc-tag, hemagglutinin A, beta-galactosidase, thymidine kinase, transferrin, (His) 6-tag, FLAG, or chloramphenicol acetyl transferase may be added to the ferritin gene to label the ferritin protein with the tag, and preferably myc-tag, but is not limited thereto. The tag protein is expressed along with the ferritin protein, and antibodies capable of detecting the tag expression may be used to detect the expression of ferritin protein.

In another embodiment, the present invention provides a transgenic mouse for expressing human ferritin in a tissue non-specific manner, which is transformed with the vector prepared, by operably linking a human ferritin gene to a cytomegalovirus early enhancer element and a β-actin promoter, or a cell or tissue isolated therefrom. Preferably, the vector may be a vector represented, by the cleavage map of FIG. 1.

The "promoter including a cytomegalovirus early enhancer and a β-actin promoter" of the present invention may be, one of the modified cytomegalovirus (CMV) promoters, a hybrid promoter including a cytomegalovirus early enhancer, a β-actin promoter, a chimeric intron, exon 1 and a part of exon 2 of a rabbit β-globin gene, but it can be variously modified according to the purpose. In the present invention, the promoter was suitably modified to be used as an expression vector for the transgenic mouse. Any modification is possible, as long as the constitution of the prompter such as a restriction enzyme site does not affect the promoter activity.

In the present invention, preferably, the β-actin prompter may be a human β-actin promoter, a shrimp β-actin promoter, a chicken β-actin prompter, a rock bream β-actin promoter or the like. To prepare the promoter including the cytomegalovirus early enhancer and the β-actin promoter, a chicken β-actin promoter may be used as a β-actin promoter in the present invention, and a CAG promoter including the cytomegalovirus early enhancer and the chicken β-actin promoter may be used. The CAG promoter is a promoter used to drive high levels of gene expression in a mammalian expression vector. Therefore, the human ferritin regulated, by the CAG promoter can be overexpressed in all cells and tissues of mouse, thereby being expressed in a tissue non-specific manner.

Figure 5:
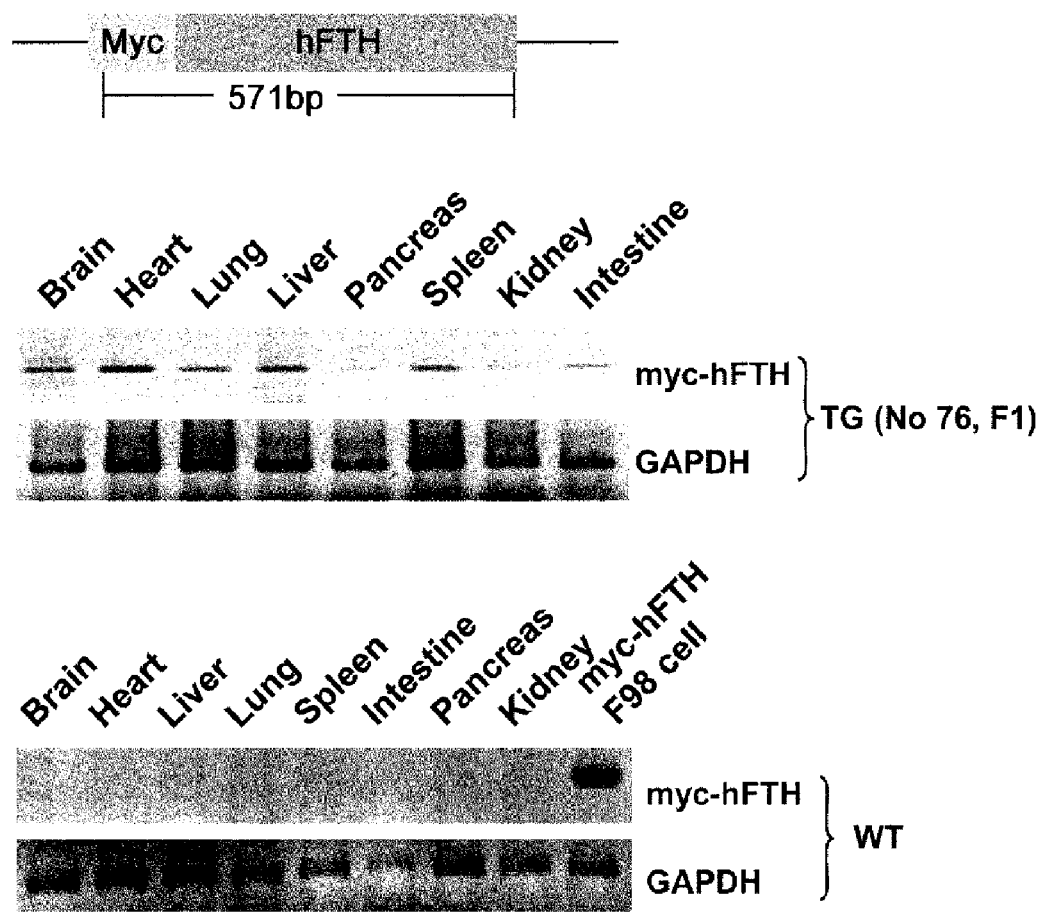
FIG. 5 shows the results of RT-PCR analysis of myc-hFTH transgene expression in various tissues of myc-hFTH transgenic mouse (TG) and wild-type mouse (WT), in which the expression of myc-hFTH transgene was detected in the brain, heart, lung, liver, pancreas, spleen, kidney and intestine of the transgenic mouse whereas no expression was detected in the wild-type mouse.
Figure 6:
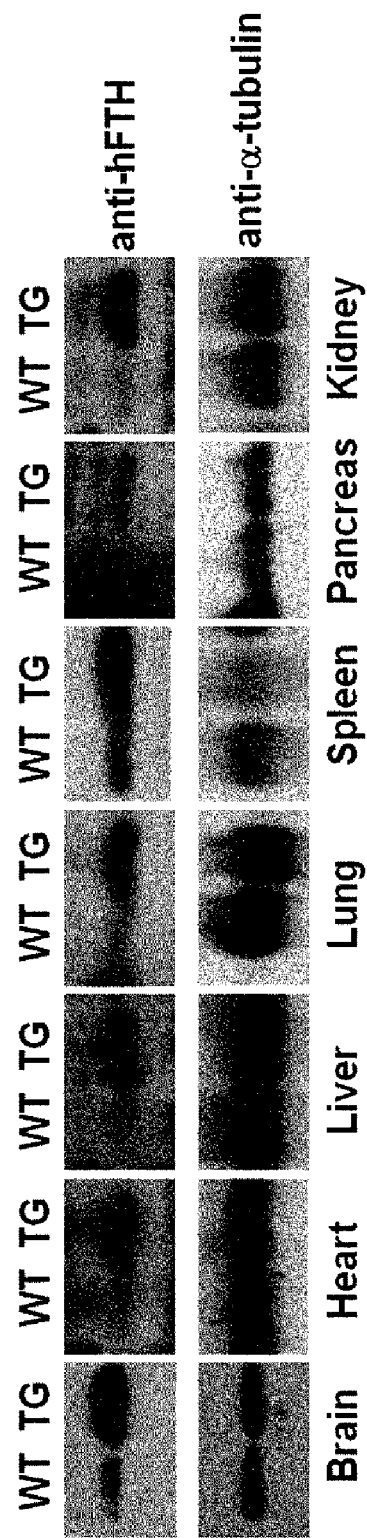
FIG. 6 shows the results of Western blot, analysis of myc-hFTH transgene expression in various tissues of myc-hFTH transgenic mouse (TG) and wild-type mouse (WT), in which the expression of myc-hFTH protein was detected in the tissues of TG as compared with WT.

According to one specific embodiment, the present inventors performed RT-PCR and Western blotting analysis using the tissues and cells of transgenic mouse and wild-type mouse in order to examine expression of human ferritin gene by the CAG promoter including the cytomegalovirus early enhancer and the chicken β-actin promoter. As a result, high expression levels of the human ferritin were observed in various tissues such as brain, heart, lung, liver, pancreas, spleen, kidney, intestine or the like of transgenic mouse (FIGS. 5 and 6).

These results demonstrate that the transgenic mouse transformed with the vector of the present invention is able to express human ferritin in a tissue non-specific manner. In addition, the cells or tissues isolated from, the mouse are able to express human ferritin in a tissue non-specific manner, thereby being used for monitoring.

As used herein, the term "transformation" refers to a process in which an organism's genotype is changed as a result of the uptake of exogenous DNA. Methods for transformation can be suitably selected from various techniques known, in the art, for example, microinjection, electroporation, particle bombardment, sperm-mediated gene transfer, viral infection, direct muscle injection, insulator, and transposon. In the present invention, transformation may be preferably performed by microinjection of the expression vector including the human ferritin gene into a fertilized, egg of mouse.

In the present invention, the strain used for the transgenic mouse includes C57BL/6n, BCF hybrid, FVB/n or the like. Among them, an inbred line strain, C57BL/6 is preferred, because it is easy and convenient for breeding.

In still another embodiment, the present invention provides a method for generating a transgenic mouse for expressing human ferritin in a tissue non-specific manner, comprising the steps of 1) preparing a vector including the cytomegalovirus early enhancer, the β-actin promoter, and the human ferritin gene; and 2) transfecting fertilized eggs with the expression vector.

In the method for generating the transgenic mouse of the present invention, the production method further includes the step of transferring fertilized eggs with the expression vector into foster mothers. In addition, the production method may further include the step of performing PCR or Southern blot using the genomic DNA isolated, from the toe of the generated transgenic mouse so as to examine the insertion of human ferritin in the genomic DNA.

Figure 4:
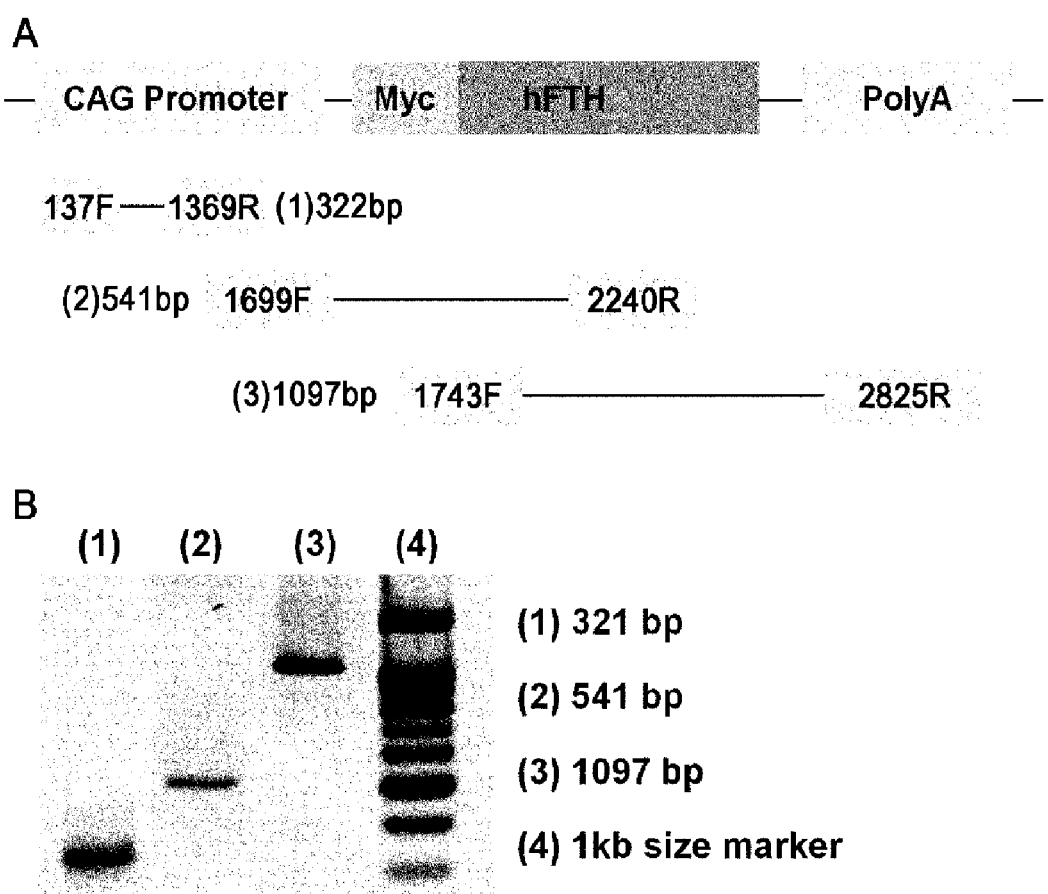
FIG. 4 shows genotyping of myc-hFTH transgenic mice, in which (A) is a schematic illustration showing the specific primer region for performing genomic PCR, and (B) shows a detection of genomic PCR products (321, 541, and 1097 bp) specific to the myc-hFTH transgene.

According to one specific embodiment, 4-week old superovulated C57BL/6 female mice were used for the collection of fertilized, eggs, and 10-12-week old ICR female mice were served as foster mothers. The collection of pronuclear-stage eggs, culturing the embryos and DNA microinjection were carried out according to standard protocol. Pronuclear microinjection was performed, under a. Nikon Diaphot. Transgenic mouse lines (C57BL/6-myc-hFTH) were analyzed by genomic PCR. Genomic DNA isolated, from, mouse toe lysate was typically used for genotype determination. Genomic DNA was extracted, rising standard proteinase K digestion and phenol/chloroform extraction to perform the genomic PCR. Insertion of human ferritin gene in the genomic DNA was observed in the toe tissue of the transgenic mouse transformed with the vector including the cytomegalovirus early enhancer, the β-actin promoter, and the human ferritin gene, compared, to that of the wild-type mouse (FIG. 4).

In still another embodiment, the present invention relates to a method for monitoring cell or tissue therapy using the transgenic mouse of the present invention.

The transgenic mouse of the present invention ubiquitously expresses human ferritin, and thus can be used as an MR reporter and as a model of human ferritin-based, molecular imaging for cell or tissue therapy. Preferably, the monitoring method may be achieved, by performing MRI.

As described above, the transgenic mouse of the present invention ubiquitously expresses human ferritin and thus can be used for monitoring the effects of cell therapy in various cells. Preferably, the transgenic mouse of the present invention may be used to monitor therapeutic effects of the brain cells, heart cells, liver cells, spleen cells, lung cells, pancreas cells, kidney cells, stem, cells or immune cells, but is not limited, thereto.

Further, the transgenic the present invention ubiquitously expresses human ferritin and thus can be used for monitoring the effects of tissue therapy in various tissues. Preferably, the transgenic mouse of the present invention may be used to monitor therapeutic effects of brain tissues, heart tissues, liver tissues, spleen tissues, lung tissues, pancreas tissues, intestine tissues, or kidney tissues, but is not limited thereto.

According to one specific embodiment, in vivo MRI of the wild-type mice and the transgenic mice expressing human ferritin by the CAG promoter including the cytomegalovirus early enhancer and the chicken b-actin promoter was performed. As a result, T2*-weighted images obtained, at 9.4 T showed a significant decrease in. T2* value in the liver and brain of transgenic mice, compared to the wild-type mice (FIG. 9). In the TEM results, iron deposition was observed in various tissues (FIG. 8), and cell therapy could be monitored.

In still another embodiment, the present invention provides the use of a transgenic mouse for monitoring cell or tissue therapy, in which the transgenic mouse is transformed with the vector prepared by operably linking a human ferritin gene to a cytomegalovirus early enhancer element and a β-actin promoter, and thus ubiquitously expresses human ferritin.

Hereinafter, the present invention will be described in more detail with reference to Examples. However, these Examples are for illustrative purposes only, and the invention is not intended to be limited, by these Examples.

EXAMPLE 1

Construction of Recombinant Human Ferritin Heavy Polypeptide (myc-hFTH, 597 bp)

The recombinant human ferritin heavy polypeptide (myc-tagged hFTH, myc-hFTH) gene fragment was obtained from LentiM1.141-myc/hFTH (Accession number BG073750) by PCR amplification using oligonucleotide primers (forward; CGGAATTCGCCACCATGGAACAA (SEQ ID NO. 2), reverse; CGGAATTCTTAGCTTTCATTATCACT (SEQ ID NO. 3)). EcoRI restriction enzyme sites were added onto each 5' region of the primer. For construction of the plasmid vector expressing myc-hFTH under the control of β-actin promoter (FIG. 1), the PCR product (597 bp) was digested with EcoRI and inserted into a pCAGGS vector (Addgene, Cambridge, Mass.). The myc-hFTH-pCAGGS clone inserts were manually sequenced using sequenase version 2.0 kit (Amersham, USA). This sequence was confirmed using the blast searcher (FIG. 2). The myc-hFTH-pCAGGS plasmid was digested with SalI and HindiIII. This DNA fragments (2.9 kb) were purified by dialysis against sterile TE buffer (10 mM Tris, pH 8.0, and 1 mM EDTA) for microinjection. A final concentration of the purified DNA was 2 ng/μl.

The present inventors constructed a pCAGGS-myc-hFTH vector expressing myc-hFTH as described above. FIG. 1 showed the construction of pCAGGS-myc-hFTH vector. Myc-hFTH expression is controlled by a CAG promoter which is a combination of the cytomegalovirus (CMV) early enhancer element and chicken β-actin promoter. The CAG promoter is frequently used to drive high levels of gene expression in mammalian expression vectors. The present inventors used, the pCAGGS vector which contains the CAG promoter and the rabbit globulin poly (A) (Rb-Glob Poly (A)). The myc-hFTH was inserted in a. EcoRI-EcoRI site available to insert a gene of interest into a pCAGGS vector under the control of the CMV promoter. The mouse c-myc gene was tagged at the N-terminal of hFTH for recombination of myc-hFTH. The myc-hFTH sequence was additionally bound with the EcoRI recognition site, and digested with EcoRI to prepare 597 bp, which is represented by SEQ ID NO. 1. The identity of the cloned cDNA was confirmed by sequencing (FIG. 2).

EXAMPLE 2

Transfection of HEK293 Cells and Confirmation

HEK293 cells were transfected with the myc-hFTH-pCAGGS vector using Lipofectamine (Invitrogen, Carlsbad, Calif.) according to the manufacturer's instructions. The Lenti-myc-hFTH vector was used, as a control. 24 hours after transfection, Western blotting of cell lysates was performed in order to confirm the myc-hFTH expression.

Figure 3:
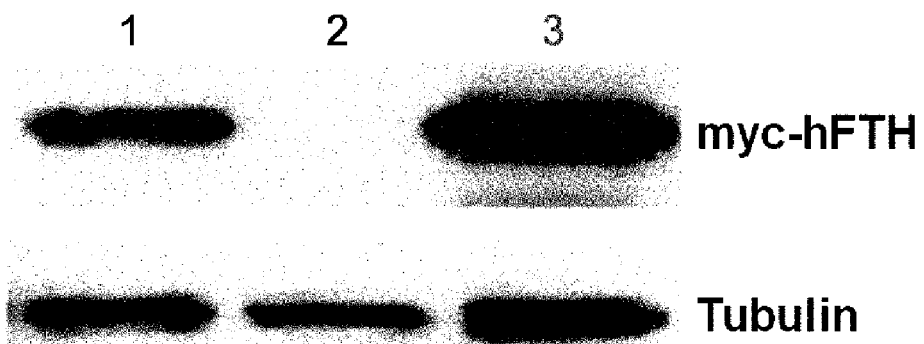
FIG. 3 shows expression of myc-hFTH in HEK293 cells transfected with the pCAGGS-myc-hFTH vector, in which myc-hFTH expression in HEK293 cells was observed by Western blot after transduction for 24 hours.

As a result, myc-hFTH expression was observed in HEK293 cells (FIG. 3).

EXAMPLE 3

Mouse Experiment

C57BL/6 and ICR mice were supplied, from the Center for Animal Resource and Development of Seoul National University. Animal experiment was conducted in the Center for Animal Resource and Development of Seoul National University. 4 to 20 week-old laboratory mice were maintained in the individual ventilation cage rack (Thoren caging systems, PA, USA) at 24±2° C. and 50%±5% humidity with a 12/12 (light/dark) cycle. Mice were given an irradiated mouse feed (Purina Korea, Seoul, Korea) and 2 ppm chloride added reverse osmosis water.

EXAMPLE 4

Generation of Transgenic Mouse and Genotyping

Transgenic mice were generated using a standard procedure in Center for Animal Resource and Development of Seoul National University. 4-week old superovulated. C57BL/6 female mice were used, for the collection of fertilized, eggs, and 10-12-week old ICR female mice were served as the foster mothers. The collection of pronuclear-stage eggs, culturing the embryos and DNA microinjection using the vector of FIG. 1 constructed in Example 1 were carried out according to standard, protocol. Briefly, after removing the cumulus cells of eggs, the eggs were placed in a microdrop of M16 medium which was covered with paraffin oil, and cultured in a $CO_2$ incubator until they were used for the microinjection. Microdrop of the M2 medium containing zygotes and that of the DNA injecting buffer (10 mM Tris-HCl (pH 8.0), 1 mM EDTA) or the DNA-enzyme mixture were placed separately on a culture dish and covered, with mineral oil. Pronuclear microinjection was performed under a Nikon Diaphot inverted, microscope with Nomarski differential interference contrast optics. All mice were raised and kept under specific pathogen free (SPF) conditions and supplied from the Center for Animal Resource and Development in Korea. Transgenic mouse lines (C57BL/6-myc-hFTH) were analysed by genomic PCR. Genomic DNA isolated from mouse toe lysate is typically used for genotype determination. Genomic DNA was extracted using standard proteinase K digestion and phenol/chloroform extraction for performing the genomic PCR. The primers specific to the promoter, myc-hFTH and poly A sequences used in genomic PCR are listed, in the following Table 1,

TABLE 1

| Primer | Sequence | SEQ ID NO. | Size |
|---|---|---|---|
| 1375F | 5'-CGCAGGGACTTCCTTTGTCC-3' | 4 | 321 bp |
| 1369R | 5'-ACAACAACCAGCACGTTGCC-3' | 5 | |
| 1699F | 5'-AACGTGCTGGTTGTTGTGCT-3' | 6 | 541 bp |
| 2240R | 5'-CGTGGTCACCCAATTCTTTG-3' | 7 | |
| 1743F | 5'-TCATCTCAGAAGAGGATCTG-3' | 8 | 1097 bp |
| 2825R | 5'-GGGACAGCTATGACTGGGAGT-3' | 9 | |

According to the above described method, the present inventors generated transgenic mice expressing the myc-tagged human ferritin heavy polypeptide under the control of a CAG promoter. Mouse genotyping was performed by genomic PCR. The specific primer sequences for performing the genomic PCR in the regions of CAG promoter, myc-hFTH and rabbit β-globin poly(A) were designed. (FIG. 4A and Table 1). As a result, the PCR products (321, 541, and 1097 bp) specific to the myc-hFTH transgene were detected (FIG. 4B).

EXAMPLE 5

RT-PCR Analysis

To investigate the expression of myc-hFTH trans gene in various tissues (brain, heart, lung, liver, pancreas, spleen, kidney, intestine), RT-PCR was performed, using the tissues of transgenic and wild-type mice.

Total RNA was extracted from various frozen tissues (brain, heart, lung, liver, pancreas, spleen, kidney, intestine) of transgenic and wild-type mice using Trizol reagent (Invitrogen, Carlsbad, Calif.), and treated with RNase-free DNase I (Invitrogen). Total RNA were used to generate the first-strand cDNA by using Superscript III (Invitrogen) and Oligo (dT) primers. The primers specific to the myc-hFTH and the mouse GAPHD sequence used, for RT-PCR are listed in the following Table 2.

TABLE 2

| Primer | Sequence | SEQ ID NO. | Size |
|---|---|---|---|
| Myc-hFTH F | 5'-ACTCATCTCAGAAGAGGATC-3' | 10 | 571 bp |
| Myc-hFTH R | 5'-GCTTTCATTATCACTGTCTC-3' | 11 | |

As shown in FIG. 5, the transcripts of myc-hFTH transgene were detected in many tissues of transgenic mice. In contrast, no expression was detected, in those of the wild-type. These results indicate that the transgenic mouse transformed with the vector of the present invention is able to ubiquitously express the ferritin gene.

EXAMPLE 6

Western Blot Analysis

To detect the presence of recombinant human ferritin (myc-hFTH), various tissues (brain, heart, lung, liver, pancreas, spleen, kidney, intestine) were homogenized in lysis buffer (20 mM Tris-HCl, pH 7.5, 150 mM NaCl, 1 mM EDTA, 1 mM $Na_3VO_4$, 50 mM NaF, 1.0% Triton X-100, 0.5% deozycholate, and 0.1% SF3; Sigma), with a protease inhibitor mixture (Complete; Roche Applied Science, Indianapolis, Ind.). Lysates containing equal amounts of protein were loaded, electrophoresed on a 15% SBS PAGE (Invitrogen, Carlsbad, Calif.) and transferred to a nitrocellulose membrane (Millipore, Billerica, Mass.). The recombinant myc-tagged hFTH polypeptides were detected, using antibodies against myc (Santa Cruz Biotechnology, Santa Cruz, Calif.) or human specific FTH (Sigma. St. Louis, Mo.). The relative quantification of myc-hFTH expression between multiple samples was achieved by normalization against mouse tubulin.

As a result, it was found that myc-hFTH proteins were overexpressed in the brain, heart, liver, lung, spleen, pancreas, and kidney of transgenic mice (FIG. 6). These results indicate that the transgenic mouse transformed, with the vector of the present invention is able to ubiquitously express the recombinant human ferritin protein (myc-hFTH).

EXAMPLE 7

Histological Analysis

Wild-type and transgenic mice were studied at same ages. After anesthesia, mice were decapitated, and organs were removed and fixed with 10% formalin in 0.1 M phosphate buffer, pH 7.2 (Sigma). Each organ was embedded in paraffin and sectioned. The prepared paraffin sections (4 μm thickness) were dewaxed, hydrated, treated with 0.01% protease XXIV (Sigma) in phosphate-buffered saline for 20 minutes at 37° C. and stained, with hematoxylin and eosin. Prussian blue iron staining was used to assay for iron accumulation. Immunohistochemical staining was performed by using primary antibodies against the human specific FTH (Santa Cruz Biotechnology) and myc (Santa Cruz Biotechnology).

Figure 7:
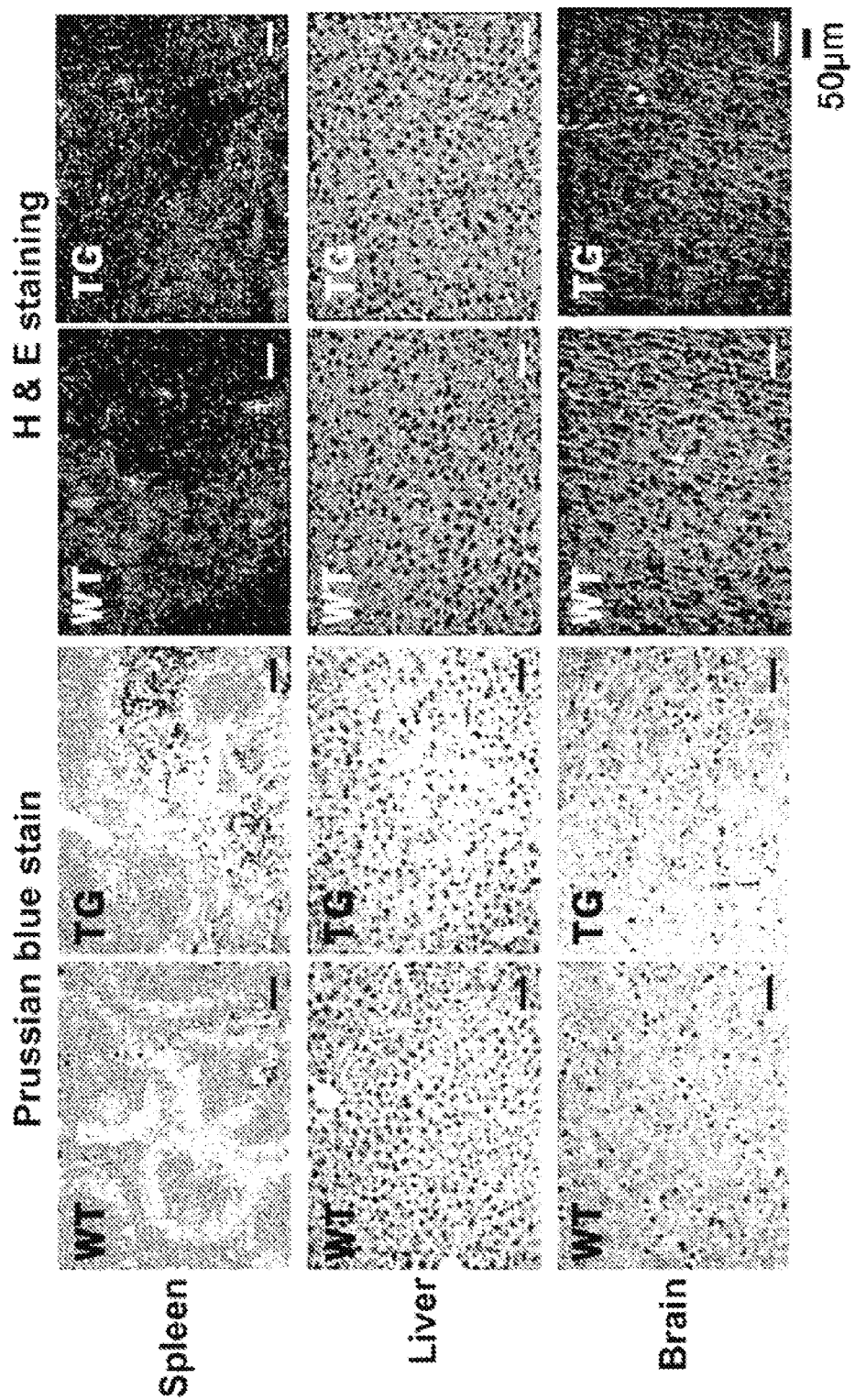
FIG. 7 shows the results of Prussian blue staining and H&F staining of the spleen, liver and brain of myc-hFTH transgenic mouse (TG) and wild-type mouse (WT), in which iron deposition was observed in the spleens of WT and TG.

Prussian blue staining and H&E staining, and myc-hFTH immunohistological staining results of the spleen, liver and brain of myc-hFTH transgenic mouse (TG) and wild-type mouse (WT) were observed by the above described Prussia blue staining and H&E staining method. Iron deposition was observed in the spleen of WT and TG, and more accumulation was observed in TG, Ferric iron accumulation in the spleen of the WT and myc-hFTH transgenic mice was examined. As a result, the iron accumulation was not observed in the levels of endogenous mouse FTH (FIG. 7). It is suggested that the ferric iron detected is probably sequestered within myc-hFTH inclusions.

EXAMPLE 8

Transmission Electron Microscopy (TEM)

The spleen, liver and brain tissue sections were obtained from 12-week-old mye-hFTH transgenic mouse (TG) and wild-type mouse (WT). Transmission electron microscopy (TEM) images of the spleen, liver and brain tissues were examined.

Figure 8:
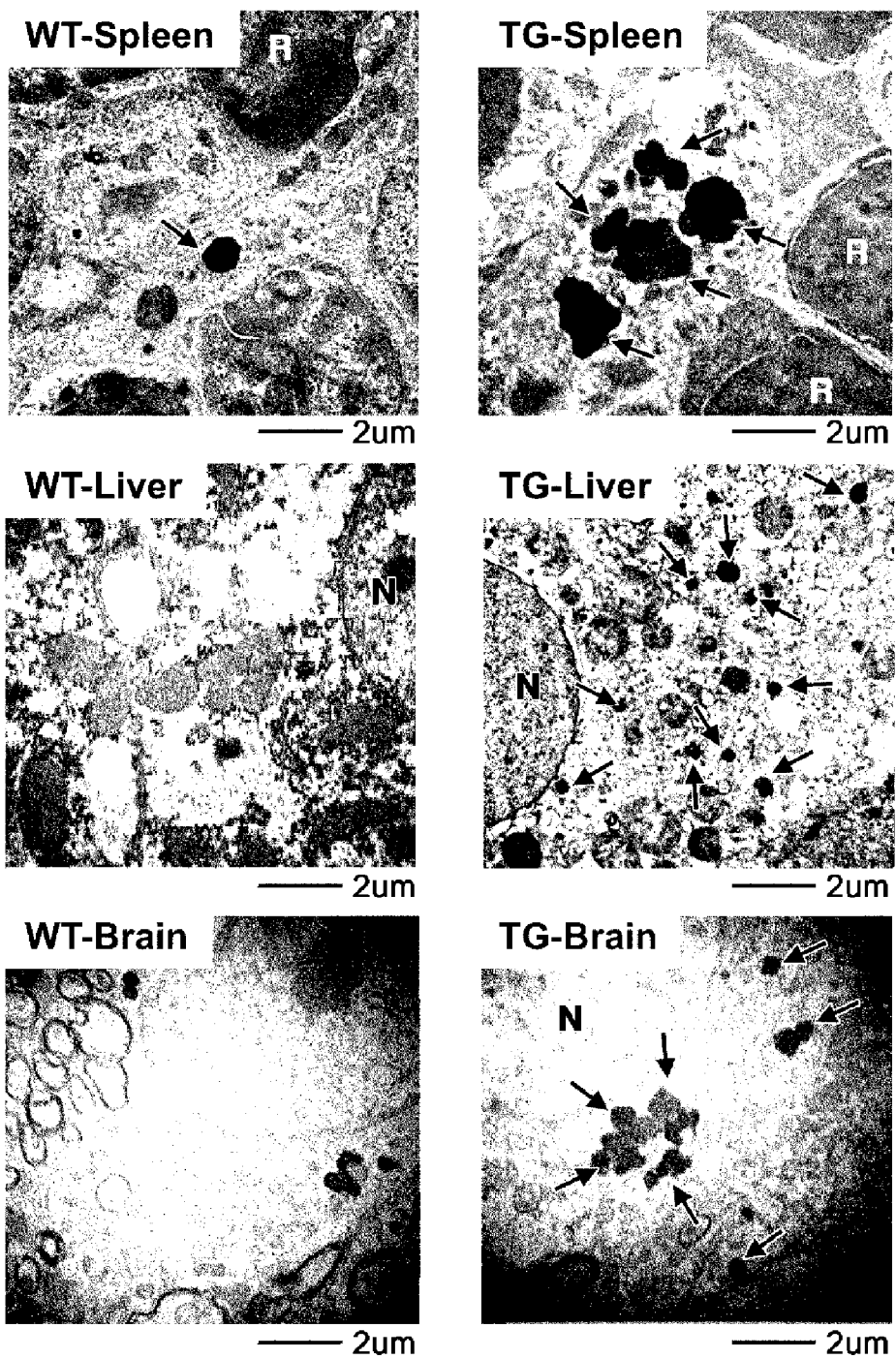
FIG. 8 shows transmission electron microscopy (TEM) images of the spleen, liver and brain, in which the spleen, liver and brain tissue sections were obtained, from a 12-week-old myc-hFTH transgenic mouse (TG) and a wild-type mouse (WT), and large ferritin inclusions were observed in the tissues of transgenic mouse and the arrows indicate intracytoplasmic iron depositions.

As a result, large ferritin inclusions were observed, in the tissues of transgenic mouse (FIG. 8). The arrows indicate intracytoplasmic iron depositions. These results indicate that expression of recombinant human ferritin, protein (myc-hFTH) in various tissues of the transgenic mouse of the present invention can be monitored by transmission electron microscopy.

EXAMPLE 9

MRI (Magnetic Resonance Imaging) Analysis and Post-Data Processing

All MRI studies were conducted on a 9.4 T Bruker Biospec scanner (Bruker Biospin, Ettlingen, Germany). For both brain and abdominal (liver and kidney) imaging, a transmit-only volume coil (Bruker Biospin, Ettlingen, Germany) was used for excitation. For signal reception 4-channel, dedicated mouse and rat brain surface coils (Bruker Biospin, Ettlingen, Germany) were used for brain and abdominal imaging, respectively. To stabilize the body temperature of the mice during the MR experiments, an animal warming system (Bruker Biospin, Ettlingen, Germany) was used, which consists of a warm water (39° C.) reservoir with a pump and hoses placed underneath the animal bed. For both brain and abdomen, an 8-point T2* mapping was performed, using a multiple gradient echo sequence (MGE). For abdominal imaging, data was collected with fat saturation and respiratory gating. The eight echo times (TEs) ranged from 3.12 to 34.41 ms with an echo spacing of 4.47 ms. Other imaging parameters common for brain and abdomen are: repetition time (TR)=5000 ms, matrix size=256×256, slice thickness=1 mm, excitation flip angle=90°, number of averages=1. For brain imaging, the typical field-of-view (FOV) and number of slices were 2.2× 2.2 mm$^2$ and 14, respectively. For abdominal imaging, they were 3.5×3.5 mm$^2$ and 17.

All post-data processing was performed using MATLAB™ (MathWorks Inc., Natick, USA). For each slice, regions of interest (ROIs) were defined in the image acquired at the shortest TE, and T2* was estimated on a pixel-by-pixel basis by using a routine least-squares fitting algorithm.

In vivo MRI of myc-hFTH transgenic mice and wild-type mice was performed, according to the above described method. As a result, color coded T2*-weighted images obtained at 9.4 T showed a significant decrease in T2* value in the river and brain of transgenic mice, compared to the wild-type mice (FIGS. 9a and 9b).

EFFECT OF THE INVENTION

According to the present invention, human ferritin could be used as an MR reporter, and the transgenic mice of the present invention would be an available model of human ferritin-based molecular imaging in which to study potential therapies for the cell and tissue graft, and also used for monitoring cell and tissue therapies.

What is claimed is:

1. A recombinant vector for expressing human ferritin in a tissue non-specific manner, comprising: a CAG promoter, a myc-tagged human ferritin gene of SEQ ID NO. 1 and a rabbit globulin poly(A) that are operably linked to each other, and wherein the recombinant vector is represented by a cleavage map of FIG. 1.

2. A transgenic mouse, a cell or tissue isolated therefrom for expressing human ferritin in a tissue non-specific manner, which is transformed with the recombinant vector of claim 1, wherein the recombinant vector comprises a CAG promoter, a myc-tagged human ferritin gene of SEQ ID NO. 1 and a rabbit globulin poly(A) that are operably linked to each other, and wherein the recombinant vector is represented by a cleavage map of FIG. 1.

3. The transgenic mouse, or the cell or tissue isolated therefrom according to claim 2, wherein the transformation is performed by a method selected from the group consisting of microinjection, electroporation, particle bombardment, sperm-mediated gene transfer, viral infection, direct muscle injection, insulator, and transposon.

4. A method for generating a transgenic mouse for expressing human ferritin in a tissue non-specific manner, comprising the steps of:
   1) preparing the recombinant vector of claim 1, which comprises a CAG promoter, a myc-tagged human ferritin gene of SEQ ID NO. 1 and a rabbit globulin poly(A) that are operably linked to each other, and which is represented by a cleavage map of FIGS. 1; and
   2) transfecting fertilized eggs of a mouse with the recombinant vector.

5. A method for monitoring cell or tissue therapy using the transgenic mouse, a cell or tissue isolated therefrom of claim 2 wherein the transgenic mouse is transformed with a recombinant vector, and wherein the recombinant vector comprises a CAG promoter, a myc-tagged human ferritin gene of SEQ ID NO. 1 and a rabbit globulin poly(A) that are operably linked to each other and is represented by a cleavage map of FIG. 1.

6. The method according to claim 5, wherein the cell is selected from the group consisting of brain cells, heart cells, liver cells, spleen cells, lung cells, pancreas cells, kidney cells, stem cells and immune cells.

7. The method according to claim 5, wherein the tissue is selected from the group consisting of brain tissues, heart tissues, liver tissues, spleen tissues, lung tissues, pancreas tissues, intestine tissues, and kidney tissues.

8. The method according to claim 5, wherein the monitoring is achieved by performing MRI (magnetic resonance imaging).

9. The method according to claim 5, wherein the transformation is performed by a method selected from the group consisting of microinjection, electroporation, particle bombardment, sperm-mediated gene transfer, viral infection, direct muscle injection, insulator, and transposon.

* * * * *